(12) United States Patent
Kupelian et al.

(10) Patent No.: US 11,083,816 B2
(45) Date of Patent: Aug. 10, 2021

(54) SOFT AND DURABLE NONWOVEN WEB

(71) Applicant: Kimberly-Clark Worldwide, Inc., Neenah, WI (US)

(72) Inventors: Mark G. Kupelian, Atlanta, GA (US); Lei Huang, Duluth, GA (US); John H. Conrad, Alpharetta, GA (US); Jeffrey J. Krueger, Roswell, GA (US); Ray A. Sterling, Woodstock, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 540 days.

(21) Appl. No.: 15/517,540

(22) PCT Filed: Nov. 18, 2014

(86) PCT No.: PCT/US2014/066114
§ 371 (c)(1),
(2) Date: Apr. 7, 2017

(87) PCT Pub. No.: WO2016/080960
PCT Pub. Date: May 26, 2016

(65) Prior Publication Data
US 2017/0304481 A1    Oct. 26, 2017

(51) Int. Cl.
*A61F 13/15*    (2006.01)
*A61L 15/22*    (2006.01)
(Continued)

(52) U.S. Cl.
CPC ....... *A61L 15/225* (2013.01); *A61F 13/51121* (2013.01); *A61F 13/51401* (2013.01);
(Continued)

(58) Field of Classification Search
CPC ........ A61L 15/225; A61L 15/20; A61L 15/24; A61F 13/51121; A61F 2013/15357;
(Continued)

(56) References Cited

U.S. PATENT DOCUMENTS

| 3,338,992 A | 8/1967 | Kinney |
| 3,341,391 A | 9/1967 | Kinney |

(Continued)

FOREIGN PATENT DOCUMENTS

| EP | 2 479 331 A1 | 7/2012 |
| EP | 2671992 | 12/2013 |

(Continued)

OTHER PUBLICATIONS

Russian Search Report dated May 21, 2018, 2 pages.
(Continued)

*Primary Examiner* — Jacqueline F Stephens
(74) *Attorney, Agent, or Firm* — Dority & Manning, P.A.

(57) ABSTRACT

A nonwoven web that contains a plurality of fibers formed from a polyolefin composition is provided. The polyolefin composition contains a rigid propylene polymer that has a relatively high melting temperature and modulus of elasticity, which can provide good strength and durability to the nonwoven web. The polyolefin composition also contains a ductile propylene polymer that has a relatively high melt flow index, which can help achieve relatively fine fibers that minimize the stiffness of the web. In addition to a rigid and ductile polymer, the polyolefin composition also contains a slip additive (e.g., fatty acid derivative). Among other things, such an additive can even further enhance the overall softness of the composition.

21 Claims, 1 Drawing Sheet

(51) Int. Cl.
*A61F 13/511* (2006.01)
*A61F 13/514* (2006.01)
*D04H 1/4291* (2012.01)
*A61L 15/24* (2006.01)
*A61L 15/20* (2006.01)
*C08L 23/12* (2006.01)
*D01F 6/46* (2006.01)

(52) U.S. Cl.
CPC .............. *A61L 15/20* (2013.01); *A61L 15/24* (2013.01); *C08L 23/12* (2013.01); *D01F 6/46* (2013.01); *D04H 1/4291* (2013.01); *A61F 2013/15357* (2013.01); *A61F 2013/51147* (2013.01); *A61F 2013/51452* (2013.01); *C08L 2203/02* (2013.01); *C08L 2203/12* (2013.01); *C08L 2205/025* (2013.01); *D10B 2509/026* (2013.01)

(58) Field of Classification Search
CPC . A61F 2013/51147; A61F 2013/51452; C08L 2203/02; C08L 2203/12; C08L 23/12; C08L 2205/025; D01F 6/46; D04H 1/4291
See application file for complete search history.

(56) References Cited

U.S. PATENT DOCUMENTS

| | | | |
|---|---|---|---|
| 3,485,706 A | 12/1969 | Evans | |
| 3,502,538 A | 3/1970 | Peterson | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 3,855,046 A | 12/1974 | Hansen et al. | |
| 4,215,682 A | 8/1980 | Kubik et al. | |
| 4,340,563 A | 7/1982 | Appel et al. | |
| 4,375,718 A | 3/1983 | Wadsworth et al. | |
| 4,592,815 A | 6/1986 | Nakao | |
| 4,668,566 A | 5/1987 | Braun | |
| 4,704,116 A | 11/1987 | Enloe | |
| 4,778,460 A | 10/1988 | Braun et al. | |
| 4,789,592 A | 12/1988 | Taniguchi et al. | |
| 4,795,668 A | 1/1989 | Krueger et al. | |
| 4,874,659 A | 10/1989 | Ando et al. | |
| 4,965,122 A | 10/1990 | Morman | |
| 4,981,747 A | 1/1991 | Morman | |
| 5,057,368 A | 10/1991 | Largman et al. | |
| 5,069,970 A | 12/1991 | Largman et al. | |
| 5,108,820 A | 4/1992 | Kaneko et al. | |
| 5,162,074 A | 11/1992 | Hills | |
| 5,192,606 A | 3/1993 | Proxmire et al. | |
| 5,226,992 A | 7/1993 | Morman | |
| 5,277,976 A | 1/1994 | Hogle et al. | |
| 5,336,545 A | 8/1994 | Morman | |
| 5,336,552 A | 8/1994 | Strack et al. | |
| 5,382,400 A | 1/1995 | Pike et al. | |
| 5,401,446 A | 3/1995 | Tsai et al. | |
| 5,466,410 A | 11/1995 | Hills | |
| 5,486,166 A | 1/1996 | Bishop et al. | |
| 5,490,846 A | 2/1996 | Ellis et al. | |
| 5,539,056 A | 7/1996 | Yang et al. | |
| 5,596,052 A | 1/1997 | Resconi et al. | |
| 5,620,779 A | 4/1997 | Levy et al. | |
| 5,652,194 A | 7/1997 | Dyer et al. | |
| 5,702,377 A | 12/1997 | Collier, IV et al. | |
| D390,708 S | 2/1998 | Brown | |
| 5,766,737 A | 6/1998 | Willey et al. | |
| 5,843,057 A | 12/1998 | McCormack | |
| 5,855,999 A | 1/1999 | McCormack | |
| 5,883,026 A | 3/1999 | Reader et al. | |
| 5,908,598 A | 6/1999 | Rousseau et al. | |
| 5,931,823 A | 8/1999 | Stokes et al. | |
| 5,932,497 A | 8/1999 | Morman et al. | |
| 5,962,112 A | 10/1999 | Haynes et al. | |
| 5,997,981 A | 12/1999 | McCormack et al. | |
| 6,002,064 A | 12/1999 | Kobylivker et al. | |
| 6,015,764 A | 1/2000 | McCormack et al. | |
| 6,037,281 A | 3/2000 | Mathis et al. | |
| 6,060,638 A | 5/2000 | Paul et al. | |
| D428,267 S | 7/2000 | Romano, III et al. | |
| 6,093,665 A | 7/2000 | Sayovitz et al. | |
| 6,111,163 A | 8/2000 | McCormack et al. | |
| 6,150,002 A | 11/2000 | Varona | |
| 6,200,669 B1 | 3/2001 | Marmon et al. | |
| 6,365,088 B1 | 4/2002 | Knight et al. | |
| 6,461,457 B1 | 10/2002 | Taylor et al. | |
| 6,500,563 B1 | 12/2002 | Datta et al. | |
| 6,663,611 B2 | 12/2003 | Blaney et al. | |
| 7,060,867 B2 | 6/2006 | Jameson | |
| 7,320,948 B2 | 1/2008 | Morman et al. | |
| 8,647,741 B2 | 2/2014 | Katayama et al. | |
| 8,980,964 B2 | 3/2015 | Topolkaraev et al. | |
| 2004/0110442 A1 | 6/2004 | Rhim et al. | |
| 2005/0054255 A1 | 3/2005 | Morman et al. | |
| 2005/0059941 A1 | 3/2005 | Baldwin et al. | |
| 2005/0106978 A1 | 5/2005 | Cheng et al. | |
| 2006/0151914 A1 | 7/2006 | Gerndt et al. | |
| 2006/0183860 A1* | 8/2006 | Mehta | ..................... C08L 23/10 525/191 |
| 2009/0061185 A1 | 3/2009 | Hisamoto | |
| 2009/0111347 A1 | 4/2009 | Peng et al. | |
| 2010/0168704 A1 | 7/2010 | Thomas et al. | |
| 2015/0368836 A1 | 12/2015 | Koori et al. | |

FOREIGN PATENT DOCUMENTS

| | | | |
|---|---|---|---|
| RU | 2125860 C1 | 2/1999 | |
| RU | 2457290 C2 | 7/2012 | |
| WO | WO-03040442 A1 * | 5/2003 | ............... C07F 7/00 |
| WO | WO 2015/075631 | 5/2015 | |
| WO | WO 2015/075632 A1 | 5/2015 | |

OTHER PUBLICATIONS

Supplementary European Search Report dated Mar. 21, 2018, 9 pages.
International Search Report and Written Opinion for PCT/US2014/066114 dated Jul. 27, 2015, 15 pages.
International Preliminary Report of Patentability Corresponding to Application No. PCT/US2014/0666114 dated Dec. 29, 2015.
Russian Office Action Corresponding to Application No. 2017118032 dated May 21, 2018.
Australian Office Action Corresponding to Application No. 2013312048 dated Mar. 1, 2019.

* cited by examiner

SOFT AND DURABLE NONWOVEN WEB

RELATED APPLICATION

The present application is the national stage entry of International Patent Application No. PCT/US2014/066114 having a filing date of Nov. 18, 2014, which is incorporated herein in its entirety by reference thereto.

BACKGROUND OF THE INVENTION

Nonwoven webs or fabrics are desirable for use in a variety of products such as disposable diapers and other personal hygiene products. For example, in a disposable diaper, it is highly desirable to have nonwoven components that are both soft and strong. Backsheets, for instance, are often formed from a polypropylene nonwoven web laminated to a breathable film made from linear low density polyethylene. One of the problems with conventional backsheets, however, is that they generally lack a soft, cloth-like feel. The polypropylene nonwoven web, for instance, can be relative rigid in nature and have a rough feel on its surface. For these reasons, various attempts have been made to improve the softness of the nonwoven web through mechanical post treatments. For example, one technique that has been attempted involves reducing the degree of thermal bonding (e.g., decreasing the size or distance between bond sites) in the nonwoven web. Unfortunately, however, this can lead to an increased degree of abrasion (e.g., fuzzing or lint). Because abrasion resistance correlates to fuzzing, known methods of nonwoven web production generally result in a tradeoff between the fuzzing and softness properties of the nonwoven web:

As such, a need currently exists for a nonwoven web that can exhibit a soft and cloth-like feel without a substantial reduction in durability (e.g., abrasion resistance) or strength.

SUMMARY OF THE INVENTION

In accordance with one embodiment of the present invention, a nonwoven web is disclosed that comprises a plurality of fibers formed from a polyolefin composition. The polyolefin composition contains at least one rigid propylene polymer, at least one ductile propylene polymer, and at least one slip additive. Further, the ductile propylene polymer has a melt flow index of greater than about 1000 grams per 10 minutes, as determined at a load of 2160 grams and at 230° C. in accordance with ASTM D1238-13.

Other features and aspects of the present invention are described in more detail below.

BRIEF DESCRIPTION OF THE DRAWING

A full and enabling disclosure of the present invention, including the best mode thereof, directed to one of ordinary skill in the art is set forth more particularly in the remainder of the specification, which makes reference to the appended FIGURE in which.

Repeat use of reference characters in the present specification and drawing is intended to represent same or analogous features or elements of the invention.

DETAILED DESCRIPTION OF REPRESENTATIVE EMBODIMENTS

Definitions

As used herein, the term "fibers" generally refer to elongated extrudates that may be formed by passing a polymer through a forming orifice, such as a die. Unless noted otherwise, the term "fibers" includes discontinuous fibers having a definite length (e.g., stable fibers) and substantially continuous filaments. Substantially filaments may, for instance, have a length much greater than their diameter, such as a length to diameter ratio ("aspect ratio") greater than about 15,000 to 1, and in some cases, greater than about 50,000 to 1.

As used herein the term "nonwoven web" generally refers to a web having a structure of fibers that are interlaid, but not in an identifiable manner as in a knitted fabric. Examples of suitable nonwoven webs include, but are not limited to, meltblown webs, spunbond webs, bonded carded webs, airlaid webs, coform webs, hydraulically entangled webs, and so forth.

As used herein, the term "spunbond" web generally refers to a nonwoven web containing substantially continuous filaments formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al.

As used herein, the term "meltblown" web or facing generally refers to a nonwoven web containing fibers formed by a process in which a molten thermoplastic material is extruded through a plurality of fine, usually circular, die capillaries as molten fibers into converging high velocity gas (e.g., air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, et al.

DETAILED DESCRIPTION

Reference now will be made in detail to various embodiments of the invention, one or more examples of which are set forth below. Each example is provided by way of explanation, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention cover such modifications and variations.

Generally speaking, the present invention is directed to a nonwoven web that contains a plurality of fibers formed from a polyolefin composition. The polyolefin composition contains a rigid propylene polymer that has a relatively high melting temperature and modulus of elasticity, which can provide good strength and durability to the nonwoven web. Although the rigid propylene polymer has a relatively stiff feel, which is not ideal, the present inventors have nevertheless surprisingly discovered that through the use of certain components in the polyolefin composition, the resulting nonwoven web can achieve a soft and ductile feel. More particularly, the polyolefin composition contains a ductile propylene polymer that has a relatively high melt flow index of more than about 1,000 grams per 10 minutes, in some embodiments from about 1,500 to about 5,000 grams per 10 minutes, and in some embodiments, from about 1,600 to about 3,000 grams per 10 minutes, determined at a load of 2160 grams and at a temperature of 230° C. in accordance with ASTM D1238-13 (or ISO 1133). The present inventors have discovered that ductile polymers with such a relatively low melt viscosity (i.e., a high melt flow index) can help achieve relatively fine fibers that minimize the stiffness of the web. For example, the fibers of the nonwoven web may have an average size (e.g., diameter) of about 100 micrometer or less, in some embodiments from about 0.1 microns to about 50 microns, and in some embodiments, from about 0.5 microns to about 40 microns. The fibers may likewise have a denier of about 6 or less, in some embodiments about 3 or less, and in some embodiments, from about 0.5 to about 2. In addition to a rigid and ductile polymer, the polyolefin composition also contains a slip additive (e.g., fatty acid derivative). Among other things, such an additive can even further enhance the overall softness of the composition.

Various embodiments of the present invention will now be described in more detail.

I. Polyolefin Composition

A. Rigid Propylene Polymer

As noted, the polyolefin composition used to form the nonwoven web contains a rigid propylene polymer, which may have a relatively high melting temperature and modulus of elasticity. For example, the rigid propylene polymer may have a melting temperature of from about 145° C. to about 200° C., in some embodiments from about 150° C. to about 180° C., and in some embodiments, from about 155° C. to about 170° C., and a modulus of elasticity of from about 800 to about 4,000 MPa, in some embodiments from about 1,000 to about 3,000 MPa, and in some embodiments, from about 1,200 to about 2,500 MPa, as determined in accordance with ASTM D638-10. The rigid propylene polymer may also have a melt flow index of from about 15 to about 100 grams per 10 minutes, in some embodiments from about 20 to about 80 grams per 10 minutes, and in some embodiments, from about 25 to about 50 grams per 10 minutes, determined at a load of 2160 grams and at 230° C., as determined in accordance with ASTM D1238-13 (or ISO 1133).

Any of a variety of propylene polymers having the characteristics noted above may generally be employed in the present invention. In one particular embodiment, for instance, the propylene polymer is an isotactic or syndiotactic homopolymer or copolymer (e.g., random or block) containing about 10 wt. % or less of co-monomers (e.g., α-olefins), and in some embodiments, about 2 wt. % or less. The term "syndiotactic" generally refers to a tacticity in which a substantial portion, if not all, of the methyl groups alternate on opposite sides along the polymer chain. On the other hand, the term "isotactic" generally refers to a tacticity in which a substantial portion, if not all, of the methyl groups are on the same side along the polymer chain. Such polymers are typically formed using a Zeigler-Natta catalyst, either alone or in combination with a small amount of an α-olefin co-monomer. Isotactic polymers, for instance, typically have a density in the range of from about 0.88 to 0.94 g/cm$^3$, and in some embodiments, from about 0.89 to 0.91 g/cm$^3$, such as determined in accordance with ASTM 1505-10. Commercially available rigid propylene homopolymers may include, for instance, Metocene™ MF650Y and MF650X, which are available from Basell Polyolefins, as well as PP 3155, which is available from Exxon Mobil. Other examples of suitable propylene polymers may be described in U.S. Pat. No. 6,500,563 to Datta, et al.; U.S. Pat. No. 5,539,056 to Yang, et al.; and U.S. Pat. No. 5,596,052 to Resconi, et al.

Rigid propylene polymers generally constitute from about 75 wt. % to about 99.5 wt. %, in some embodiments from about 80 wt. % to about 99 wt. %, and in some embodiments, from about 85 wt. % to 98 wt. % of the polymer content of the polyolefin composition. Likewise, the rigid propylene polymers may constitute from about 75 wt. % to about 99.5 wt. %, in some embodiments from about 80 wt. % to about 99 wt. %, and in some embodiments, from about 85 wt. % to 98 wt. % of the entire polyolefin composition.

B. Ductile Propylene Polymer

In addition to having a relatively high melt flow index (i.e., low viscosity) as noted above, the ductile propylene polymer may also have a relatively low modulus of elasticity in comparison with the rigid propylene polymer, which further reduces the overall stiffness of the polyolefin composition. For example, the ratio of the modulus of elasticity of the rigid propylene polymer to that of the ductile propylene polymer is typically from about 1 to about 50, in some embodiments from about 2 to about 40, and in some embodiments, from about 5 to about 30. The modulus of elasticity of the ductile propylene polymer may, for instance, range from about 1 to about 500 MPa, in some embodiments from about 5 to about 300 MPa, and in some embodiments, from about 10 to about 100 MPa, as determined in accordance with ASTM D638-10.

In addition, the ductile propylene polymer may also have a relatively low melting point and a relatively low degree of crystallinity. For example, the melting temperature of the ductile polymer may be from about 40° C. to about 120° C., in some embodiments from about 50° C. to about 100° C., and in some embodiments, from about 55° C. to about 85° C. Likewise, the degree of crystallinity of the polymer may be from about 1% to about 35%, in some embodiments from about 3% to about 20%, and in some embodiments, from about 5% and about 25%. Through the use of a ductile propylene polymer having a relatively low melting temperature and degree of crystallinity, the window of temperatures at which the polyolefin composition begins to melt can be broadened, which thereby improves its ability to become adequately bonded other layers, such as described a film or another nonwoven web as described in more detail below. This melting temperature window of the polyolefin composition can be characterized using differential scanning calorimetry as the width ($\Delta W_{f1/2}$) at the half height of the endothermic melting peak. As a result of the present invention, for instance, $\Delta W_{f1/2}$ may be about 5° C. or more, in some embodiments about 8° C. or more, and in some embodiments, from about 10° C. to about 20° C. The melting temperature of the polyolefin composition may likewise range from about 100° C. to about 180° C., in some embodiments from about 120° C. to about 170° C., and in some embodiments, from about 150° C. to about 160° C. The width at the half height of the endothermic peak ($\Delta W_{f1/2}$), melting temperature (i.e., peak of the endothermic curve), and degree of crystallinity may all be determined as is well known in the art using differential scanning calorimetry ("DSC") in accordance with ASTM D-3417.

Any of a variety of propylene polymers having the characteristics noted above may generally be employed in the present invention. In one particular embodiment, for instance, the ductile propylene polymer is a low crystalline homopolymer or copolymer (e.g., random or block) containing about 10 wt. % or less of co-monomers (e.g., α-olefins), and in some embodiments, about 2 wt. % or less. Such polymers are typically formed using a metallocene catalyst, either alone or in combination with a small amount of an α-olefin co-monomer. Examples of suitable metallocene catalysts for low crystalline propylene polymers may be described in U.S. Patent Publication No. 2012/0208422 to Koori, et al. For instance, such metallocene catalysts may be obtained from a combination of a promoter and a transition metal compound that form a cross-linked structure via two cross-linking groups. Suitable promoters may include, for instance, dimethylanilinium tetrakis(pentafluorophenyl) borate, triethylammonium tetraphenylborate, tri(n-butyl) ammonium tetraphenylborate, trimethylammonium tetraphenylborate, tetraethylamrnonium tetraphenylborate, methyl(tri-n-butyl)ammonium tetraphenylborate, benzyl(tri-n-butyl)ammonium tetraphenylborate, aluminoxane (e.g., methylalurninoxane, ethylaluminoxane, isobutylaluminoxane, etc.), and so forth. Suitable transition metal compounds may likewise include (1,2'-dimethylsilylene) (2,1'-dimethylsilylene)bis(3-n-butylindenyl)zirconium dichloride, (1,2'-dimethylsilyiene)(2,1'-dimethylsilylene)bis(3-trimethyisilylmethylindenyl)zirconium dichloride, (1,2'-dimethylsilylene)(2,1'-dimethylsilylene)bis(3-phenylindenyl)zirconium dichloride, (1,2'-dimethylsilylene)(2,1'-dimethylsilylene)bis(4,5-benzoindenyl)zirconium dichloride, (1,2'-dimethylsilylene)(2,1'-dimethylsilylene)bis(4-isopropylindenyl)zirconium dichloride, (1,2'-dimethylsilylene)(2,1'-dimethylsilylene)bis(5,6-dimethylindenyl)zirconium dichloride, (1,2'-dimethylsilylene)(2,1'-dimethylsilylene)bis(4,7-di-isopropylindenyl)zirconium dichloride, (1,2'-dimethylsilylene)(2,1'-dimethylsilylene)bis(4-phenylindenyl)zirconium dichloride, (1,2'-dimethylsilylene)(2,1'-dimethylsilylene)bis(3-methyl-4-isopropylindenyl)zirconium dichloride, (1,2'-dimethylsilylene)(2,1'-dimethylsilyiene)bis(5,6-benzoindenyl)zirconium dichloride, (1,2'-dimethylsilylene) (2,1'-isopropylidene)-bis(indenyl)zirconium dichloride, (1,2'-dimethylsilylene)(2,1'-isopropylidene)-bis(3-methylindenyl)zirconium dichloride, (1,2'-dimethylsilyene) (2,1'-isopropylidene)-bis(3-isopropylindenyl) dichloride, (1,2'-dimethylsilylene) (2,1'-isopropylidene)-bis(3-n-butylindenyl)zirconium dichloride, and (1,2'-dimethylsilylene)(2,1'-isopropylidene)-bis(3-trimethylsilylmethylin-denyl)zirconium dichloride, etc., as well as transition metal compounds produced by substituting zirconium in the aforementioned compounds with titanium or hafnium.

The resulting ductile propylene polymer typically has a density in the range of from 0.85 to 0.91 g/cm³, and in some embodiments, from about 0.85 to 0.089 g/cm³, such as determined in accordance with ASTM 1505-10. The ductile propylene polymer may also have a weight average molecular weight of from about 10,000 to about 200,000 grams per mole, in some embodiments from about 30,000 to about 100,000 grams per mole, and in some embodiments, from about 40,000 to about 80,000 grams per mole, as well as a polydispersity index (weight average molecular weight divided by number average molecular weight) of about 4 or less, and in some embodiments, about 3 or less. Commercially available examples of such metallocene-catalyzed propylene polymers may include, for instance, L-MODU™ S400, which is available from Idemitsu Kosan.

Ductile propylene polymers generally constitute from about 0.1 wt. % to about 20 wt. %, in some embodiments from about 0.2 wt. % to about 15 wt. %, and in some embodiments, from about 1 wt. % to 12 wt. % of the polymer content of the polyolefin composition. Likewise, the ductile propylene polymers may constitute from about 0.1 wt. % to about 20 wt. %, in some embodiments from about 0.5 wt. % to about 15 wt. %, and in some embodiments, from about 1 wt. % to 12 wt. % of the entire polyolefin composition.

C. Slip Additive

A slip additive is also employed in the polyolefin composition. If desired, the weight ratio of ductile propylene polymers to slip additives may be selectively controlled in the present invention to help achieve the desired degree of softness and tactility without adversely impacting the overall durability and strength of the composition. More specifically, the weight ratio of ductile propylene polymers to slip additives typically ranges from about 1 to about 50, in some embodiments from about 1.5 to about 40, and in some embodiments, from about 2 to about 30. While the actual amount may generally vary, slip additives typically constitute from about 0.01 wt. % to about 6 wt. %, in some embodiments from about 0.1 wt. % to about 5 wt. %, and in some embodiments, from about 0.5 wt. % to about 3 wt. % of the polyolefin composition.

Slip additives generally reduce internal friction within a composition and can include materials such as amides, waxes, fluorocompounds, fatty acids, fatty acid derivatives, etc., as well as combinations thereof. Fatty acid derivatives are particularly suitable for use in the composition and may include, for instance, fatty acid amides, fatty acid esters, fatty acid salts, and so forth. In one particular embodiment, for example, the fatty acid derivative may be a fatty acid amide. The fatty acid amide may be any suitable amide compound derived from the reaction between a fatty acid and ammonia or an amine-containing compound (e.g., a compound containing a primary amine group or a secondary amine group). The fatty acid may be any suitable fatty acid, such as a saturated or unsaturated $C_8$-$C_{28}$ fatty acid or a saturated or unsaturated $C_{12}$-$C_{28}$ fatty acid. In certain embodiments, the fatty acid may be erucic acid (i.e., cis-13-docosenoic acid), oleic acid (i.e., cis-9-octadecenoic acid), stearic acid (octadecanoic acid), behenic acid (i.e., docosanoic acid), arachic acid (i.e., arachidinic acid or elcosanoic acid), palmitic acid (i.e., hexadecanoic acid), and mixtures or combinations thereof. The amine-containing compound can be any suitable amine-containing compound, such as fatty amines (e.g., stearylamine or oleylamine), ethylenediamine, 2,2'-iminodiethanol, and 1,1'-iminodipropan-2-ol.

More particularly, the fatty acid amide may be a fatty acid amide having the structure of one of Formulae (I)-(V):

(I)

(II)

-continued (III)

(IV)

(V)

wherein, $R_{13}$, $R_{14}$, $R_{15}$, $R_{16}$, and $R_{18}$ are independently selected from $C_7$-$C_{27}$ alkyl groups and $C_7$-$C_{27}$ alkenyl groups, and in some embodiments, $C_{11}$-$C_{27}$ alkyl groups and $C_{11}$-$C_{27}$ alkenyl groups;

$R_{17}$ is selected from $C_8$-$C_{28}$ alkyl groups and $C_8$-$C_{28}$ alkenyl groups, and in some embodiments, $C_{12}$-$C_{28}$ alkyl groups and $C_{12}$-$C_{28}$ alkenyl groups; and $R_{19}$ is —$CH_2CH_2OH$ or —$CH_2CH(CH_3)OH$.

For example, the fatty acid amide may have the structure of Formula (I), where $R_{13}$ is —$CH_2(CH_2)_{10}CH$=$CH(CH_2)_7CH_3$ (erucamide), —$CH_2(CH_2)_6CH$=$CH(CH_2)_7CH_3$ (oleamide), —$CH_2(CH_2)_{15}CH_3$, —$CH_2(CH_2)_{19}CH_3$, or —$CH_2(CH_2)_{17}CH_3$. In other embodiments, the fatty acid amide may have the structure of Formula (II) where $R_{14}$ is —$CH_2(CH_2)_{10}CH$=$CH(CH_2)_7CH_3$ and $R_{15}$ is —$CH_2(CH_2)_{15}CH_3$, or where $R_{14}$ is —$CH_2(CH_2)_6CH$=$CH(CH_2)_7CH_3$ and $R_{15}$ is —$CH_2(CH_2)_{13}CH_3$. Likewise, in yet other embodiments, the fatty acid amide may have the structure of Formula (III) where $R_{16}$ is $CH_2(CH_2)_{15}CH_3$ or —$CH_2(CH_2)_6CH$=$CH(CH_2)_7CH_3$. The composition may also contain a mixture of two or more such fatty acid amides.

If desired, fatty acid esters may also be employed in the present invention. Fatty acid esters may be obtained by oxidative bleaching of a crude natural wax and subsequent esterification of a fatty acid with an alcohol. The fatty acid may be a $C_8$-$C_{28}$ fatty acid or a saturated or unsaturated $C_{12}$-$C_{28}$ fatty acid, such as described above. The alcohol may have 1 to 4 hydroxyl groups and 2 to 20 carbon atoms. When the alcohol is multifunctional (e.g., 2 to 4 hydroxyl groups), a carbon atom number of 2 to 8 is particularly desired. Particularly suitable multifunctional alcohols may include dihydric alcohol (e.g., ethylene glycol, propylene glycol, butylene glycol, 1,3-propanediol, 1,4-butanediol, 1,6-hexanediol and 1,4-cyclohexanediol), trihydric alcohol (e.g., glycerol and trimethylolpropane), tetrahydric alcohols (e.g., pentaerythritol and erythritol), and so forth. Aromatic alcohols may also be suitable, such as o-, m- and p-tolylcarbinol, chlorobenzyl alcohol, bromobenzyl alcohol, 2,4-dimethylbenzyl alcohol, 3,5-dimethylbenzyl alcohol, 2,3,5-cumobenzyl alcohol, 3,4,5-trimethylbenzyl alcohol, p-cuminyl alcohol, 1,2-phthalyl alcohol, 1,3-bis(hydroxymethyl)benzene, 1,4-bis(hydroxymethyl)benzene, pseudocumenyl glycol, mesitylene glycol and mesitylene glycerol. Fatty acid salts may also be employed, such as those formed by saponification of a fatty acid to neutralize excess carboxylic acids and form a metal salt. Saponification may occur with a metal hydroxide, such as an alkali metal hydroxide (e.g., sodium hydroxide) or alkaline earth metal hydroxide (e.g., calcium hydroxide). The resulting fatty acid salt typically includes an alkali metal (e.g., sodium, potassium, lithium, etc.) or alkaline earth metal (e.g., calcium, magnesium, etc.).

D. Optional Additives

If desired, various other additives may also be employed in the polyolefin composition as is well known in the art. Examples of such additives may include, for instance, elastomers (e.g., styrenic elastomers, olefinic elastomers, etc.), fillers, pigments, antioxidants, stabilizers (e.g., melt stabilizers, light stabilizers, heat stabilizers, etc.), surfactants, flow promoters, solid solvents, plasticizers, particulates, bonding agents, tackifiers, viscosity modifiers, etc. When employed, such additives typically constitute from about 0.001 wt. % to about 15 wt. %, in some embodiments from about 0.01 to about 10 wt. %, and in some embodiments, from about 0.1 wt. % to about 8 wt. % of the polyolefin composition.

In certain embodiments, for instance, the polyolefin composition may contain an olefinic elastomer, such as a copolymer of propylene and an α-olefin. Suitable α-olefins may be linear or branched (e.g., one or more $C_1$-$C_3$ alkyl branches, or an aryl group) and formed from olefins, such as $C_2$-$C_{20}$ α-olefins, $C_2$-$C_{12}$ α-olefins, or $C_2$-$C_8$ α-olefins. Specific examples include ethylene, butene; 3-methyl-1-butene; 3,3-dimethyl-1-butene; pentene; pentene with one or more methyl, ethyl or propyl substituents; hexene with one or more methyl, ethyl or propyl substituents; heptene with one or more methyl, ethyl or propyl substituents; octene with one or more methyl, ethyl or propyl substituents; nonene with one or more methyl, ethyl or propyl substituents; ethyl, methyl or dimethyl-substituted decene; dodecene; styrene; and so forth. Particularly desired α-olefin comonomers are ethylene, butene (e.g., 1-butene), hexene, and octene (e.g., 1-octene or 2-octene). The propylene content of the propylene/α-olefin copolymer is typically from about 60 mole % to about 99.5 mole %, in some embodiments from about 80 mole % to about 99 mole %, and in some embodiments, from about 85 mole % to about 98 mole %. The α-olefin content may likewise range from about 0.5 mole % to about 40 mole %, in some embodiments from about 1 mole % to about 20 mole %, and in some embodiments, from about 2 mole % to about 15 mole %. Generally speaking, the copolymer has a density lower than that of certain polyolefins (e.g., LLDPE), but approaching and/or overlapping that of other elastomers. For example, the density of the copolymer may be about 0.91 grams per cubic centimeter (g/cm³) or less, in some embodiments from about 0.85 to about 0.89 g/cm³, and in some embodiments, from about 0.85 g/cm³ to about 0.88 g/cm³. Such propylene copolymers are commercially available under the designations VISTAMAXX™ from ExxonMobil Chemical Co. and VERSIFY™ available from Dow Chemical Co.

II. Nonwoven Web

The fibers of the nonwoven web may generally have any of a variety of different configuration as is known in the art. For example, monocomponent and/or multicomponent fibers may be employed. Monocomponent fibers, for instance, are typically formed by extruding a polymer composition from a single extruder. Multicomponent fibers, on the other hand, are generally formed from two or more polymer compositions (e.g., bicomponent fibers) extruded from separate extruders. The polymer compositions may be arranged in substantially constantly positioned distinct zones across the cross-section of the fibers. The components may be arranged in any desired configuration, such as sheath-core, side-by-side, pie, island-in-the-sea, three island, bull's eye, or various other arrangements known in the art. Various methods for forming multicomponent fibers are described in U.S. Pat. No. 4,789,592 to Taniguchi et al. and U.S. Pat. No. 5,336,552 to Strack et al., U.S. Pat. No. 5,108,820 to Kaneko, et al., U.S. Pat. No. 4,795,668 to Kruege, et al., U.S. Pat. No. 5,382,400 to Pike, et al., U.S. Pat. No. 5,336,552 to Strack, et al., and U.S. Pat. No. 6,200,669 to Marmon, et al. Multicomponent fibers having various irregular shapes may also be formed, such as described in U.S. Pat. No. 5,277,976 to Hogle, et al., U.S. Pat. No. 5,162,074 to Hills, U.S. Pat. No. 5,466,410 to Hills, U.S. Pat. No. 5,069,970 to Largman, et al., and U.S. Pat. No. 5,057,368 to Largman, et al.

The fibers may constitute the entire fibrous component of the nonwoven web or blended with other types of fibers. When blended with other types of fibers, it is normally desired that the fibers of the present invention constitute from about 20 wt % to about 95 wt. %, in some embodiments from about 30 wt. % to about 90 wt. %, and in some embodiments, from about 40 wt. % to about 80 wt. % of a web.

Any of a variety of known techniques may be employed to form the nonwoven web. For example, in one embodiment, the nonwoven web may be formed by a spunbond process in which the polyolefin composition is fed to an extruder and extruded through a conduit to a spinneret. Spinnerets for extruding fibers are well known to those of skill in the art. For example, the spinneret may include a housing containing a spin pack having a plurality of plates stacked one on top of each other and having a pattern of openings arranged to create flow paths for the polymer composition. The spinneret may also have openings arranged in one or more rows that form a downwardly extruding curtain of fibers when the polymer composition is extruded therethrough. The process may also employ a quench blower positioned adjacent the curtain of fibers extending from the spinneret. Air from the quench air blower may quench the fibers as they are formed. A fiber draw unit or aspirator may also be positioned below the spinneret to receive the quenched fibers. Fiber draw units or aspirators for use in melt spinning polymers are well-known in the art. The fiber draw unit may include an elongate vertical passage through which the fibers are drawn by aspirating air entering from the sides of the passage and flowing downwardly through the passage. A heater or blower may supply aspirating air to the fiber draw unit, which draws the fibers and ambient air through the fiber draw unit.

The fibers may be formed into a coherent web structure by randomly depositing the fibers onto a forming surface (optionally with the aid of a vacuum) and then bonding the resulting web using any known technique, such as with an adhesive or autogenously (e.g., fusion and/or self-adhesion of the fibers without an applied external adhesive). Autogenous bonding, for instance, may be achieved through contact of the fibers while they are semi-molten or tacky, or simply by blending a tackifying resin and/or solvent with polymer composition used to form the fibers. Suitable autogenous bonding techniques may include ultrasonic bonding, thermal bonding, through-air bonding, and so forth. Typically, the resulting basis weight of each web is about 30 grams per square meter or less, in some embodiments from about 1 to about 20 grams per square meter, and in some embodiments, from about 2 to about 10 grams per square meter.

Regardless of the particular manner in which it is formed, the resulting nonwoven web may possess a high degree of abrasion, as well as enhanced strength and toughness. For example, the web may exhibit a relatively high "peak load", which indicates the maximum load to break as expressed in units of grams-force per inch. The MD peak load of the nonwoven web may, for instance, be about 2,000 grams-force ("$g_f$") or more, in some embodiments about 2,500 $g_f$ or more, and in some embodiments, from about 3,000 to about 15,000 $g_f$. The CD peak load may likewise be about 1,000 $g_f$ or more, in some embodiments about 1,200 $g_f$ or more, and in some embodiments, from about 1,500 to about 10,000 $g_f$. In addition, the nonwoven web is also capable of exhibiting improved "peak elongation" properties, i.e., the percent elongation of the nonwoven web at its peak load. For example, the nonwoven web of the present invention may exhibit a machine direction ("MD") peak elongation of about 20% or more, in some embodiments about 25% or more, and in some embodiments, from about 30% to about 70%. The nonwoven web may also exhibit a cross-machine direction ("CD") peak elongation of about 30% or more, in some embodiments about 35% or more, and in some embodiments, from about 40% to about 80%.

Of course, in addition to possessing good mechanical properties, the nonwoven web of the present invention is also soft, drapable, and tactile. One parameter that is indicative of the softness of the web is the peak load ("cup crush load") as determined according to the "cup crust" test, which is described in more detail below. More particularly, the cup crush load of the nonwoven web may, for instance, be about 200 $g_f$ or less, in some embodiments about 150 $g_f$ or less and in some embodiments, from about 5 to about 100 $g_f$. Another parameter that is indicative of the good tactile properties of the web is the static coefficient of friction in the machine or cross-machine direction. More particularly, the MD and/or CD coefficient of friction may be about 0.885 or less, in some embodiments about 0.850 or less, and in some embodiments, from about 0.500 to about 0.800. The nonwoven web also typically has a basis weight of from about 1 to about 45 grams per square meter or less, in some embodiments from about 2 to about 30 grams per square meter, and in some embodiments, from about 3 to about 20 grams per square meter.

If desired, the nonwoven web of the present invention may be applied with various treatments to impart desirable characteristics. For example, the nonwoven web may be stretched or necked in the machine and/or cross-machine directions. Suitable stretching techniques may include necking, teetering, groove roll stretching, etc. Examples of suitable stretching techniques are described in U.S. Pat. Nos. 5,336,545, 5,226,992, 4,981,747 and 4,965,122 to Morman, as well as U.S. Patent Application Publication No. 2004/0121687 to Morman, et al. Alternatively, the nonwoven web may remain relatively inextensible in at least one direction. The nonwoven web may also be subjected to other known processing steps, such as aperturing, heat treatments, etc.

Further, the web may be treated with liquid-repellency additives, antistatic agents, surfactants, colorants, antifogging agents, fluorochemical blood or alcohol repellents, lubricants, and/or antimicrobial agents. In addition, the web may be subjected to an electret treatment that imparts an electrostatic charge to improve filtration efficiency. The charge may include layers of positive or negative charges trapped at or near the surface of the polymer, or charge clouds stored in the bulk of the polymer. The charge may also include polarization charges that are frozen in alignment of the dipoles of the molecules. Techniques for subjecting a fabric to an electret treatment are well known by those skilled in the art. Examples of such techniques include, but are not limited to, thermal, liquid-contact, electron beam and corona discharge techniques. In one particular embodiment, the electret treatment is a corona discharge technique, which involves subjecting the laminate to a pair of electrical fields that have opposite polarities. Other methods for forming an electret material are described in U.S. Pat. No. 4,215,682 to Kubik, et al.; U.S. Pat. No. 4,375,718 to Wadsworth; U.S. Pat. No. 4,592,815 to Nakao; U.S. Pat. No. 4,874,659 to Ando; U.S. Pat. No. 5,401,446 to Tsai, et al.; U.S. Pat. No. 5,883,026 to Reader, et al.; U.S. Pat. No. 5,908,598 to Rousseau, et al.; U.S. Pat. No. 6,365,088 to Knight, et al.

III. Composites

Although not necessarily required, it may be advantageous to combine the nonwoven web of the present invention with one or more additional layers to form a composite. Examples of such layers may include, for instance, nonwoven webs, films, strands, etc. In one embodiment, for instance, the nonwoven web of the present invention ("first nonwoven web") may be positioned adjacent to a second nonwoven web that contains a plurality of fibers that are formed from a second polyolefin composition. The nature of the first and second nonwoven webs may vary as desired. In one embodiment, for instance, both nonwoven webs may be a spunbond web.

In embodiments such as referenced above, the second polyolefin composition may contain an ethylene polymer having a relatively low melting temperature and modulus of elasticity, which and can provide a soft feel to a surface of the composite. Ethylene polymers may, for instance, constitute about 80 wt. % or more, in some embodiments about 90 wt. % or more, and in some embodiments, from about 92 wt. % to 100 wt. % of the polymer content of the second polyolefin composition. Of course, the actual amount of such polymers may vary depending on the presence of any optional additives in the composition. Examples of such additives may include, for instance, fillers, pigments, antioxidants, stabilizers (e.g., melt stabilizers, light stabilizers, heat stabilizers, etc.), surfactants, flow promoters, solid solvents, plasticizers, particulates, bonding agents, tackifiers, viscosity modifiers, etc. When employed, additives typically constitute from about 0.001 wt. % to about 10 wt. %, in some embodiments from about 0.01 to about 8 wt. %, and in some embodiments, from about 0.1 wt. % to about 5 wt. % of the second polyolefin composition. Likewise, ethylene polymers may constitute from about 90 wt. % to about 99.999 wt. %, in some embodiments from about 92 wt. % to about 99.99 wt. %, and in some embodiments, from about 95 wt % to about 99.9 wt. % of the second polyolefin composition.

The ethylene polymer typically has a relatively low melting temperature and modulus of elasticity, which can provide the resulting nonwoven web with a relatively soft and ductile feel. For example, the ethylene polymer may have a melting temperature of from about 50° C. to about 145° C., in some embodiments from about 75° C. to about 140° C., and in some embodiments, from about 100° C. to about 135° C., and a modulus of elasticity of from about 50 to about 700 MPa, in some embodiments from about 75 to about 600 MPa, and in some embodiments, from about 100 to about 500 MPa, as determined in accordance with ASTM D638-10. The melting temperature of the entire second polyolefin composition may likewise range from about 50° C. to about 145° C., in some embodiments from about 75° C. to about 140° C., and in some embodiments, from about 100° C. to about 135° C. The modulus of elasticity of the composition may also range from about 50 to about 700 MPa, in some embodiments from about 75 to about 600 MPa, and in some embodiments, from about 100 to about 500 MPa, as determined in accordance with ASTM D638-10. The ethylene polymer may also have a melt flow index of from about 1 to about 100 grams per 10 minutes, in some embodiments from about 5 to about 50 grams per 10 minutes, and in some embodiments, from about 10 to about 40 grams per 10 minutes, determined at a load of 2160 grams and at 190° C., as determined in accordance with ASTM D1238-13 (or ISO 1133).

Any of a variety of ethylene polymers may generally be employed in the present invention, in one embodiment, for instance, the ethylene polymer may be a copolymer of ethylene and an α-olefin, such as a $C_3$-$C_{20}$ α-olefin or $C_3$-$C_{12}$ α-olefin. Suitable α-olefins may be linear or branched (e.g., one or more $C_1$-$C_3$ alkyl branches, or an aryl group). Specific examples include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are 1-butene, 1-hexene and 1-octene. The ethylene content of such copolymers may be from about 60 mole % to about 99 mole %, in some embodiments from about 80 mole % to about 98.5 mole %, and in some embodiments, from about 87 mole % to about 97.5 mole %. The α-olefin content may likewise range from about 1 mole % to about 40 mole %, in some embodiments from about 1.5 mole % to about 15 mole %, and in some embodiments, from about 2.5 mole % to about 13 mole %. The density of the polyethylene may vary depending on the type of polymer employed, but generally ranges from about 0.85 to about 0.96 grams per cubic centimeter ($g/cm^3$). Polyethylene "plastomers", for instance, may have a density in the range of from about 0.85 to about 0.91 $g/cm^3$. Likewise, "linear low density polyethylene" (LLDPE) may have a density in the range of from about 0.91 to about 0.940 $g/cm^3$; "low density polyethylene" (LDPE) may have a density in the range of from about 0.910 to about 0.940 $g/cm^3$; and "high density polyethylene" (HDPE) may have density in the range of from about 0.940 to about 0.960 $g/cm^3$, such as determined in accordance with ASTM 1505-10. LLDPE may be particularly suitable for use in the second polyolefin composition. Any of a variety of known techniques may generally be employed to form the ethylene polymer. For instance, olefin polymers may be formed using a free radical or a coordination catalyst (e.g., Ziegler-Natta). Typically, the ethylene polymer is formed from a single-site coordination catalyst, such as a metallocene catalyst.

Once formed, the first and second nonwoven webs may be laminated together to form a composite using any conventional technique, such as with an adhesive or autogenously. In one embodiment, for example, the nonwoven webs may be thermally bonded by passing the webs through a nip formed between a pair of rolls, one or both of which are heated to melt-fuse the fibers. One or both of the rolls may also contain intermittently raised bond points to provide an intermittent bonding pattern. The pattern of the raised points is generally selected so that the nonwoven laminate has a total bond area of less than about 50% (as determined by conventional optical microscopic methods), and in some embodiments, less than about 30%. Likewise, the bond density is also typically greater than about 100 bonds per square inch, and in some embodiments, from about 250 to about 500 pin bonds per square inch. Such a combination of total bond area and bond density may be achieved by bonding the web with a pin bond pattern having more than about 100 pin bonds per square inch that provides a total bond surface area less than about 30% when fully contacting a smooth anvil roll. In some embodiments, the bond pattern may have a pin bond density from about 250 to about 350 pin bonds per square inch and a total bond surface area from about 10% to about 25% when contacting a smooth anvil roll. Exemplary bond patterns include, for instance, those described in U.S. Pat. No. 3,855,046 to Hansen et al., U.S. Pat. No. 5,620,779 to Levy et al., U.S. Pat. No. 5,962,112 to Haynes et al., U.S. Pat. No. 6,093,665 to Sayovitz et al., U.S. Design Pat. No. 428,267 to Romano et al. and U.S. Design Pat. No. 390,708 to Brown.

Due to the particular thermal properties of the polyolefin compositions used to form the first and second nonwoven webs, the present inventors nave discovered that relatively low temperatures can be used to bond the webs together. For example, the bonding temperature (e.g., the temperature of the rollers) may be relatively low, such as from about 50° C. to about 165° C., in some embodiments from about 80° C. to about 160° C., and in some embodiments, from about 100° C. to about 155° C. Likewise, the nip pressure may range from about 5 to about 150 pounds per square inch, in some embodiments, from about 10 to about 100 pounds per square inch, and in some embodiments, from about 30 to about 60 pounds per square inch.

Other types of bonding techniques may also be employed in the present invention to attach the first and second nonwoven webs. In one embodiment, for example, hydraulic entangling may be employed using conventional hydraulic entangling equipment, such as described in U.S. Pat. No. 3,485,706 to Evans. Hydraulic entangling may be carried out with any appropriate working fluid, such as, for example, water. The working fluid may flow through a manifold that evenly distributes the fluid to a series of individual holes or orifices. These holes or orifices may be from about 0.003 to about 0.015 inch in diameter and may be arranged in one or more rows with any number of orifices, e.g., 30-100 per inch, in each row. However, it should also be understood that many other manifold configurations and combinations may be used. Although not held to any particular theory of operation, it is believed that the columnar jets of working fluid that directly impact the fibers of one of the webs and drive those fibers into and partially through the other web, causing the fibers to entangle and bond together. To achieve the desired entanglement, it is typically desired that hydroentangling be performed using water pressures from about 1000 to 3000 prig, and in some embodiments, from about 1200 to 1800 psig.

The resulting composite may be a two-layered material containing only the first and second nonwoven webs. In such embodiments, the first nonwoven web typically constitutes from about 20 wt. % to about 80 wt. %, in some embodiments from about 30 wt. % to about 70 wt. %, and in some embodiments, from about 40 wt. % to about 60 wt. % of the composite, and the second nonwoven web likewise constitutes from about 20 wt. % to about 80 wt. %, in some embodiments from about 30 wt. % to about 70 wt. %, and in some embodiments, from about 40 wt. % to about 60 wt. % of the composite. The nonwoven composite typically has a basis weight of from about 1 to about 45 grams per square meter or less, in some embodiments from about 2 to about 30 grams per square meter, and in some embodiments, from about 3 to about 20 grams per square meter.

Of course, it should also be understood that the nonwoven web may also be combined with other types of layers, such as a nonwoven web, film, strands, etc., either with or without the ethylene-based nonwoven web described above. In one embodiment, for example, the composite may contain three (3) or more layers, and in some embodiments, from three (3) to ten (10) layers (e.g., 3 or 5 layers). For instance, the nonwoven composite may contain an inner nonwoven layer (e.g., meltblown or spunbond) positioned between two outer nonwoven layers (e.g., spunbond). The inner nonwoven layer may be formed from an ethylene-based polyolefin composition as described above and one or both of the outer nonwoven layers may be formed in accordance with the present invention. In another embodiment, the composite may contain five (5) nonwoven layers, which includes a central nonwoven layer, two intermediate nonwoven layers overlying the central layer, and two outer nonwoven layers overlying the intermediate layers. The central layer may, for instance, be formed from the nonwoven web of the present invention and one or both of the intermediate layers may be formed from the ethylene-based polyolefin composition. If desired, the outer layers may likewise be formed from the nonwoven web of the present invention.

The composite itself may also be employed in a multi-layered laminate structure in which one or more additional layers are employed. For example, the laminate may have other configurations and possess any desired number of layers, such as a spunbond/meltblown/meltblown/spunbond ("SMMS") laminate, spunbond/meltblown ("SM") laminate, etc. In such embodiments, the composite of the present invention may desirably form on or more of the spunbond layers. In yet another embodiment, the composite may be employed in a multi-layered laminate structure in which one or more additional film layers are employed. Any known technique may be used to form a film, including blowing, casting, flat die extruding, etc. The film may be a mono- or multi-layered film. Any of a variety of polymers may generally be used to form the film layer, such as polyolefins (e.g., polyethylene, polypropylene, polybutylene, etc.); polytetrafluoroethylene; polyesters (e.g., polyethylene terephthalate, polylactic acid, etc.); polyamides (e.g., nylon); polyvinyl chloride; polyvinylidene chloride; polystyrene; and so forth. In one embodiment, for instance, the film may be formed from a polyolefin polymer, such as linear, low-density polyethylene (LLDPE) or polypropylene. Examples of predominately linear polyolefin polymers include, without limitation, polymers produced from the following monomers: ethylene, propylene, 1-butene, 4-methyl-pentene, 1-hexene, 1-octene and higher olefins as well as copolymers and terpolymers of the foregoing. In addition, copolymers of ethylene and other olefins including butene, 4-methyl-pentene, hexene, heptene, octene, decene, etc., are also examples of predominately linear polyolefin polymers.

Various additional potential processing and/or finishing steps known in the art, such as slitting, stretching, etc., may be performed without departing from the spirit and scope of the invention. For instance, the nonwoven web and/or composite may optionally be mechanically stretched in the cross-machine and/or machine directions to enhance extensibility. For example, the web and/or composite may be coursed through two or more rolls that have grooves in the CD and/or MD directions that incrementally stretch the composite in the CD and/or MD direction. Such grooved satellite/anvil roll arrangements are described in U.S. Patent Application Publication Nos. 2004/0110442 to Rhim, et al.

and 2006/0151914 to Gerndt, et al. The grooved rolls may be constructed of steel or other hard material (such as a hard rubber). Besides grooved rolls, other techniques may also be used to mechanically stretch the composite in one or more directions. For example, the web and/or composite may be passed through a tenter frame that stretches the composite. Such tenter frames are well known in the art and described, for instance, in U.S. Patent Application Publication No. 2004/0121687 to Morman, et al. The composite may also be necked, such as described above.

Similar to the nonwoven web of the present invention, as described above, the resulting composite may also possess a high degree of abrasion, as well as enhanced strength and toughness. For example, the composite may exhibit a relatively high "peak load", which indicates the maximum load to break as expressed in units of grams-force per inch. The MD peak load of the composite may, for instance, be about 2,000 grams-force ("$g_f$") or more, in some embodiments about 3,000 $g_f$ or more, and in some embodiments, from about 4,000 to about 15,000 $g_f$. The CD peak load may likewise be about 1,200 $g_f$ or more, in some embodiments about 1,500 $g_f$ or more, and in some embodiments, from about 2,000 to about 10,000 $g_f$. In addition, the nonwoven composite is also capable of exhibiting improved "peak elongation" properties, i.e., the percent elongation of the composite at its peak load. For example, the nonwoven composite of the present invention may exhibit a machine direction ("MD") peak elongation of about 20% or more, in some embodiments about 30% or more, and in some embodiments, from about 40% to about 70%. The nonwoven composite may also exhibit a cross-machine direction ("CD") peak elongation of about 35% or more, in some embodiments about 45% or more, and in some embodiments, from about 50% to about 80%. The cup crush load of the composite may also be about 200 $g_f$ or less, in some embodiments about 150 $g_f$ or less and in some embodiments, from about 5 to about 100 $g_f$. Likewise, the MD and/or CD coefficient of friction may be about 0.885 or less, in some embodiments about 0.850 or less, and in some embodiments, from about 0.500 to about 0.800.

IV. Articles

The nonwoven web and/or composite of the present invention may be used in a wide variety of applications. For example, the nonwoven web may be incorporated into an "absorbent article" that is capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, mitt wipe, and so forth; medical absorbent articles, such as garments, fenestration materials, underpads, bedpads, bandages, absorbent drapes, and medical wipes; food service wipers; clothing articles; pouches, and so forth. Materials and processes suitable for forming such absorbent articles are well known to those skilled in the art. Typically, absorbent articles include a substantially liquid-impermeable layer (e.g., backsheet), a liquid-permeable layer (e.g., topsheet, surge layer, etc.), and an absorbent core.

In certain embodiments, for example, the nonwoven web of the present invention may be used to form the topsheet and/or backsheet of the absorbent article. When used to form the backsheet, the nonwoven web may also be laminated to a film, such as described above. The film is typically liquid-impermeable and either vapor-permeable or vapor-impermeable. Films that are liquid-impermeable and vapor-permeable are often referred to as "breathable" and they typically have a water vapor transmission rate ("WVTR") of about 100 grams per square meter per 24 hours ($g/m^2/24$ hours) or more, in some embodiments from about 500 to about 20,000 $g/m^2/24$ hours, and in some embodiments, from about 1,000 to about 15,000 g $g/m^2/24$ hours. The breathable film may also be a microporous or monolithic film. Microporous films are typically formed by incorporating a filler (e.g., calcium carbonate) into the polymer matrix, and thereafter stretching the film to create the pores. Examples of such films are described, for instance, in U.S. Pat. No. 5,843,057 to McCormack; U.S. Pat. No. 5,855,999 to McCormack; U.S. Pat. No. 5,932,497 to Morman, et al.; U.S. Pat. No. 5,997,981 to McCormack, et al.; U.S. Pat. No. 6,002,064 to Kobylivker, et al.; U.S. Pat. No. 6,015,764 to McCormack, et al.; U.S. Pat. No. 6,037,281 to Mathis, et al.; U.S. Pat. No. 6,111,163 to McCormack, et al.; and U.S. Pat. No. 6,461,457 to Taylor, et al.

Regardless of how it is employed, one particularly beneficial aspect of the present invention is that the nonwoven web, which is formed from a propylene-based composition that includes a rigid propylene polymer, ductile propylene polymer, and slip additive, can be positioned so that it defines an outwardly facing surface of the absorbent article. More particularly, the unique properties of the propylene-based composition can allow it to impart a soft and cloth-like feel to an outwardly facing surface, which was conventionally only partially achievable with polyethylene materials (e.g., LLDPE breathable film) and generally not possible with polypropylene materials. Furthermore, contrary to polyethylene materials, the propylene-based nonwoven web can exhibit an improved degree of abrasion resistance and mechanical strength, making it even better served to define the outwardly facing surface of an absorbent article. When used in a backsheet, for example, the second nonwoven web may define a "garment-facing surface", which generally refers to an outwardly facing surface of an absorbent article that is intended to be disposed away from the body of a wearer during ordinary use. The surface is typically placed adjacent to the wearer's undergarments when the article is worn. Likewise, when used in a topsheet, the second nonwoven web may define a "body-facing surface", which generally refers to an outwardly facing surface of an absorbent article that is intended to be disposed toward or placed adjacent to the body of a wearer during ordinary use.

Figure 1:
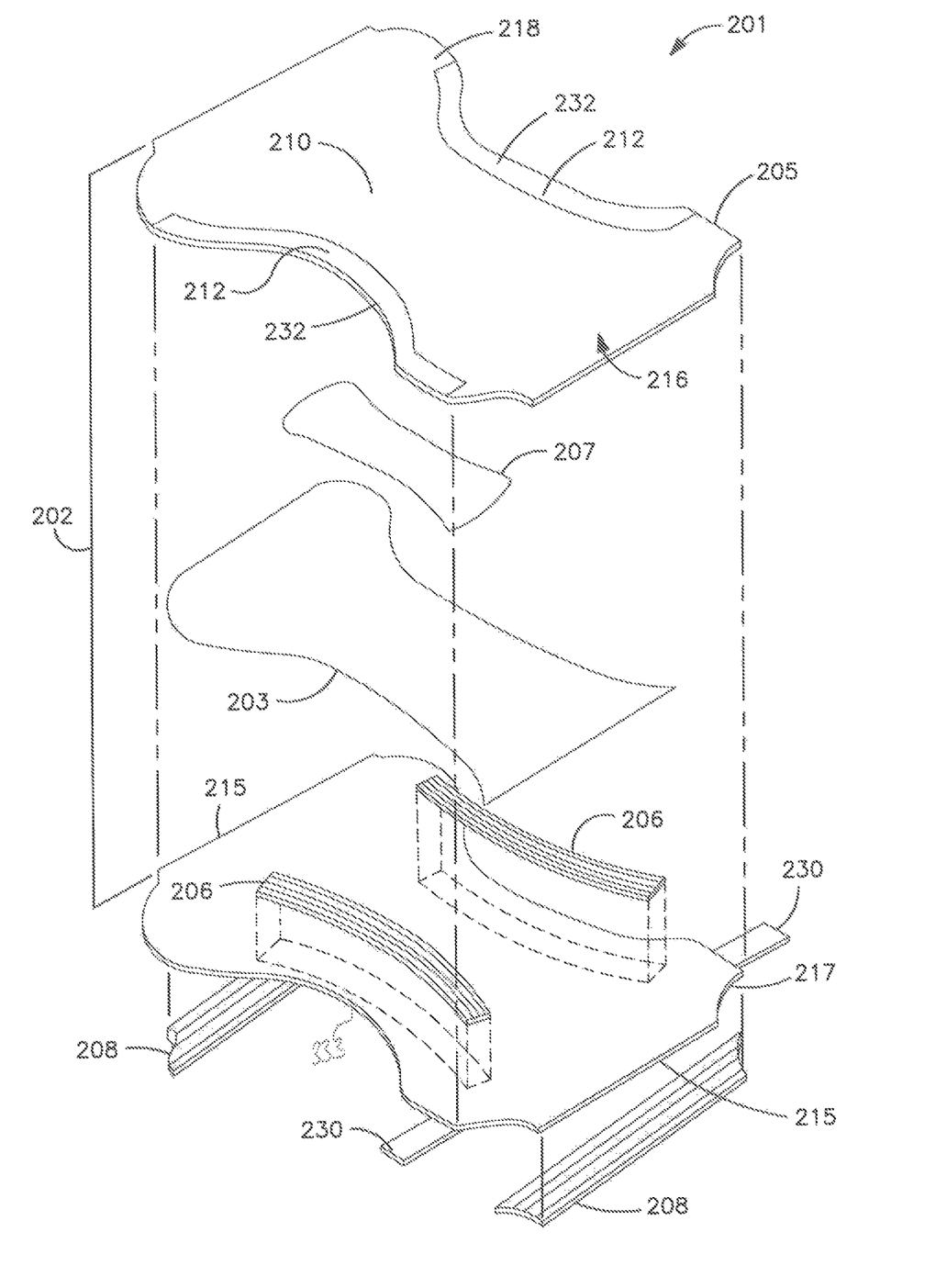
FIG. 1 is a perspective view of an absorbent article that may be formed in accordance with one embodiment of the present invention.

Various embodiments of an absorbent article that may be formed according to the present invention will now be described in more detail. Referring to FIG. 1, for instance, one embodiment of an absorbent article 201 is shown in the form of a diaper. However, as noted above, the invention may be embodied in other types of absorbent articles, such as incontinence articles, sanitary napkins, diaper pants, feminine napkins, children's training pants, and so forth. In the illustrated embodiment, the absorbent article 201 is shown as having an hourglass shape in an unfastened configuration. However, other shapes may of course be utilized, such as a generally rectangular shape, T-shape, or I-shape. As shown, the absorbent article 201 includes a chassis 202 formed by various components, including a backsheet 217, topsheet 205, absorbent core 203, and surge layer 207. It should be understood, however, that other layers may also be used in the present invention. Likewise, one or more of the layers referred to in FIG. 1 may also be eliminated in certain embodiments of the present invention.

As indicated above, the backsheet 217 may be formed from the nonwoven web of the present invention. In fact, as discussed, the nonwoven web may define a garment-facing surface 333 of the absorbent article 201. The absorbent article 201 also includes a topsheet 205. The topsheet 205 is generally employed to help isolate the wearer's skin from liquids held in the absorbent core 203. For example, the topsheet 205 may define a body-facing surface 218, which is typically compliant, soft feeling, and non-irritating to the wearer's skin. If desired, the topsheet 205 may be formed from the nonwoven web of the present invention. In fact, as discussed, the nonwoven web may be positioned so that the second nonwoven web defines the body-facing surface 218 if so desired. Alternatively, the topsheet may include a conventional a nonwoven web (e.g., spunbond web, meltblown web, or bonded carded web). Other exemplary topsheet constructions that contain a nonwoven web are described in U.S. Pat. Nos. 5,192,606; 5,702,377; 5,931, 823; 6,060,638; and 6,150,002, as well as U.S. Patent Application Publication Nos. 2004/0102750, 2005/0054255, and 2005/0059941.

As illustrated in FIG. 1, the absorbent article 201 may also include a surge layer 207 that helps to decelerate and diffuse surges or gushes of liquid that may be rapidly introduced into the absorbent core 203. Desirably, the surge layer 207 rapidly accepts and temporarily holds the liquid prior to releasing it into the storage or retention portions of the absorbent core 203. In the illustrated embodiment, for example, the surge layer 207 is interposed between an inwardly facing surface 216 of the topsheet 205 and the absorbent core 203. Alternatively, the surge layer 207 may be located on the outwardly facing surface 218 of the topsheet 205. The surge layer 207 is typically constructed from highly liquid-permeable materials. Suitable materials may include porous woven materials, porous nonwoven materials, and apertured films. In one embodiment, the surge layer 207 may also be formed from the nonwoven web of the present invention. Other examples of suitable surge layers are described in U.S. Pat. No. 5,486,166 to Ellis, et al. and U.S. Pat. No. 5,490,846 to Ellis, et al.

Besides the above-mentioned components, the absorbent article 201 may also contain various other components as is known in the art. For example, the absorbent article 201 may also contain a substantially hydrophilic wrapsheet (not illustrated) that helps maintain the integrity of the fibrous structure of the absorbent core 203. The wrapsheet is typically placed about the absorbent core 203 over at least the two major facing surfaces thereof, and composed of an absorbent cellulosic material, such as creped wadding or a high wet-strength tissue. The wrapsheet may be configured to provide a wicking layer that helps to rapidly distribute liquid over the mass of absorbent fibers of the absorbent core 203. The wrapsheet material on one side of the absorbent fibrous mass may be bonded to the wrapsheet located on the opposite side of the fibrous mass to effectively entrap the absorbent core 203. Furthermore, the absorbent article 201 may also include a ventilation layer (not shown) that is positioned between the absorbent core 203 and the backsheet 217. When utilized, the ventilation layer may help insulate the backsheet 217 from the absorbent core 203, thereby reducing dampness in the backsheet 217. Examples of such ventilation layers may include a nonwoven web laminated to a breathable film, such as described in U.S. Pat. No. 6,663,611 to Blaney, et al. If desired, such nonwoven webs may be formed in accordance with the present invention.

In some embodiments, the absorbent article 201 may also include a pair of ears (not shown) that extend from the side edges 232 of the absorbent article 201 into one of the waist regions. The ears may be integrally formed with a selected diaper component. For example, the ears may be integrally formed with the backsheet 217 or from the material employed to provide the top surface. In alternative configurations, the ears may be provided by members connected and assembled to the backsheet 217, the top surface, between the backsheet 217 and top surface, or in various other configurations.

As representatively illustrated in FIG. 1, the absorbent article 201 may also include a pair of containment flaps 212 that are configured to provide a barrier and to contain the lateral flow of body exudates. The containment flaps 212 may be located along the laterally opposed side edges 232 of the topsheet 205 adjacent the side edges of the absorbent core 203. The containment flaps 212 may extend longitudinally along the entire length of the absorbent core 203, or may only extend partially along the length of the absorbent core 203. When the containment flaps 212 are shorter in length than the absorbent core 203, they may be selectively positioned anywhere along the side edges 232 of absorbent article 201 in a crotch region 210. In one embodiment, the containment flaps 212 extend along the entire length of the absorbent core 203 to better contain the body exudates. Such containment flaps 212 are generally well known to those skilled in the art. For example, suitable constructions and arrangements for the containment flaps 212 are described in U.S. Pat. No. 4,704,116 to Enloe.

The absorbent article 201 may include various elastic or stretchable materials, such as a pair of leg elastic members 206 affixed to the side edges 232 to further prevent leakage of body exudates and to support the absorbent core 203. In addition, a pair of waist elastic members 208 may be affixed to longitudinally opposed waist edges 215 of the absorbent article 201. The leg elastic members 206 and the waist elastic members 208 are generally adapted to closely fit about the legs and waist of the wearer in use to maintain a positive, contacting relationship with the wearer and to effectively reduce or eliminate the leakage of body exudates from the absorbent article 201. The absorbent article 201 may also include one or more fasteners 230. For example, two flexible fasteners 130 are illustrated in FIG. 1 on opposite side edges of waist regions to create a waist opening and a pair of leg openings about the wearer. The shape of the fasteners 230 may generally vary, but may include, for instance, generally rectangular shapes, square shapes, circular shapes, triangular shapes, oval shapes, linear shapes, and so forth. The fasteners may include, for instance, a hook material. In one particular embodiment, each fastener 230 includes a separate piece of hook material affixed to the inside surface of a flexible backing.

The various regions and/or components of the absorbent article 201 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In the illustrated embodiment, for example, the backsheet 217 and topsheet 205 are assembled to each other and to the absorbent core 203 using an adhesive. Alternatively, the absorbent core 203 may be connected to the backsheet 217 using conventional fasteners, such as buttons, hook and loop type fasteners, adhesive tape fasteners, and so forth. Similarly, other diaper components, such as the leg elastic members 206, waist elastic members 208 and fasteners 230, may also be assembled into the absorbent article 201 using any attachment mechanism.

Although various configurations of a diaper have been described above, it should be understood that other diaper and absorbent article configurations are also included within the scope of the present invention. In addition, the present invention is by no means limited to diapers. In fact, any other absorbent article may be formed in accordance with the present invention, including, but not limited to, other personal care absorbent articles, such as training pants, absorbent underpants, adult incontinence products, feminine hygiene products (e.g., sanitary napkins, swim wear, baby wipes, and so forth; medical absorbent articles, such as garments, fenestration materials, underpads, bandages, absorbent drapes, and medical wipes; food service wipers; clothing articles; and so forth.

The present invention may be better understood with reference to the following examples.

Test Methods

Thermal Properties:

The melting temperature and degree of crystallinity of a material may be determined by differential scanning calorimetry ("DSC") in accordance with ASTM D-3417. The differential scanning calorimeter was a DSC Q 2000 (T-zero cell0, which may be outfitted with a liquid nitrogen cooling accessory and with a UNIVERSAL ANALYSIS 2000 (version 4.6.6) analysis software program, both of which are available from T.A. Instruments Inc. To avoid directly handling the samples, tweezers or other tools may be used. The sample (e.g., 4 milligrams) may be placed into an aluminum pan and weighed to an accuracy of 0.01 milligram on an analytical balance. A lid may be crimped over the material sample onto the pan. Typically, the sample is placed directly in the weighing pan. The differential scanning calorimeter may be calibrated using an indium metal standard and a baseline correction was performed, as described in the operating manual for the differential scanning calorimeter. A sample may be placed into the test chamber of the differential scanning calorimeter for testing, and an empty pan may be used as a reference. All testing may be run with a 55-cubic centimeter per minute nitrogen (industrial grade) purge on the test chamber. The heating and cooling program may be a 2-cycle test that begins with an equilibration of the chamber to −50° C., followed by a first heating period at a heating rate of 10° C. per minute to a temperature of 225° C., equilibration of the sample at 225° C. for 3 minutes, and a first cooling period at a cooling rate of 10° C. per minute to a temperature of −50° C., a second heating period at a heating rate of 10° C. per minute to a temperature of 225° C., equilibration of the sample at 225° C. for 3 minutes, and then a second cooling period at a cooling rate of 10° C. per minute to a temperature of −50° C. All testing may be conducted in an inert gas atmosphere (e.g., helium).

The results may be evaluated using the UNIVERSAL ANALYSIS 2000 analysis software program, which identifies and quantifies the endothermic and exothermic peaks, and the areas under the peaks on the DSC plots. The melting temperature is determined using an automatic inflection calculation. The areas under the peaks on the DSC plots are determined in terms of joules per gram of sample (J/g). For example, the heat of fusion of a sample ($\Delta H_f$) is determined by integrating the area of the endothermic peak. The area values are determined by converting the areas under the DSC plots (e.g. the area of the endotherm) into the units of joules per gram (J/g) using computer software. The exothermic heat of crystallization ($\Delta H_c$) can be determined during the first cooling cycle. If desired, the % crystallinity may also be calculated as follows:

$$\% \text{ crystallinity} = 100*(A-B)/C$$

wherein,

A is the sum of endothermic peak areas during the heating cycle (J/g);

B is the sum of exothermic peak areas during the heating cycle (J/g); and

C is the heat of fusion for the selected polymer where such polymer has 100% crystallinity (J/g). The areas under any exothermic peaks encountered in the DSC scan due to insufficient crystallinity may also be subtracted from the area under the endothermic peak to appropriately represent the degree of crystallinity.

Tensile Properties:

The strip tensile strength values were determined in substantial accordance with ASTM Standard D-5034. Specifically, a sample was cut or otherwise provided with size dimensions that measured 3 inches (76.2 millimeters) (width)×6 inches (152.4 millimeters) (length). A constant-rate-of-extension type of tensile tester was employed. The tensile testing system was a Sintech Tensile Tester, which is available from MTS Corp. of Eden Prairie, Minn. The tensile tester was equipped with TESTWORKS 4.08B software from MTS Corporation to support the testing. An appropriate load cell was selected so that the tested value fell within the range of 10-90% of the full scale load. The sample was held between grips having a front and back face measuring 1 inch (25.4 millimeters)×3 inches (76 millimeters). The grip faces were rubberized, and the longer dimension of the grip was perpendicular to the direction of pull. The grip pressure was pneumatically maintained at a pressure of 60 to 80 pounds per square inch. The tensile test was run at a 20 inches per minute rate with a gauge length of 4 inches and a break sensitivity of 40%. Three samples were tested along the machine-direction ("MD") and three samples were tested by along the cross direction ("CD"). In addition, the ultimate tensile strength ("peak load"), and peak elongation was also recorded.

Martindale Abrasion:

This test can measure the relative resistance of a sample to abrasion according to Worldwide Strategic Partners ("WSP") Standard Test No. 20.5 (08). A circular specimen of 165 mm±6.4 mm in diameter with an area of 18.258 sq mm is subjected to a requested number of cycles (10 or 60) with an abradant under a pressure of 9 kilopascais (kPa). The abradant is a 36 inch by 4 inch by 0.05 thick silicone rubber wheel reinforced with fiberglass having a rubber surface hardness 81A Durorneter, Shore A of 81±9. The specimen is examined for the presence of surface fuzzing (fiber lofting), pilling (small clumps of fibers), roping, delamination or holes and assigned a numerical rating of 1, 2, 3, 4, or 5 based on comparison to a set of standard photographs similarly numbered, with "1" showing the greatest wear and "5" the least. The test is carried out with a Martindale Wear and Abrasion Tester such as Model No. 103 or 403 from James H. Heal & Company, Ltd. of West Yorkshire, England.

Cup Crush Softness:

The softness of a sample may also be measured according to the "cup crush" test according to WSP Standard Test No. 402.0 (09), which evaluates softness by measuring the peak load ("cup crush load") that is required for a hemi-spherically shaped foot (4.5 cm diameter) to crush a sample (23 cm×23 cm) into an inverted cup shape (approximately 6.5 cm diameter×6.5 cm tall) while the cup-shaped sample remains surrounded by a cylinder (approximately 6.5 cm diameter) to maintain uniform deformation. An average of 10 readings is used. The foot and cup are aligned to avoid contact between the cup walls and the foot which could affect the readings. The peak load is measured while the foot is descending at a rate of about 380 mm per minute and is measured in grams. The cup crush test also yields a value for the total energy required to crush a sample (the cup crush energy), which is the energy from the start of the test to the peak load point, i.e. the area under the curve formed by the load in grams on the one axis and the distance the foot travels in millimeters on the other. Cup crush energy is therefore reported in g*mm. Lower cup crush values indicate a softer material. One suitable device for measuring cup crush is a model PTD-G-500 load cell (500 gram range) available from the Schaevitz Company of Pennsauken, N.J. Static and Dynamic Coefficient of Friction:

Coefficient of Friction testing may be performed in accordance with ASTM D 1894-08 using a high gloss smooth vinyl tile sliding surface. A sled, which has the test specimen attached thereto, may be pulled over a high gloss smooth vinyl tile surface. The test specimen and the vinyl tile surface are in surface-to-surface contact with each other. The coefficient of friction value is defined as the measure of the relative difficulty when the surface of the test specimen slid over the fixed vinyl tile surface. The "static" coefficient of friction is the highest instantaneous value obtained to begin movement between the surfaces and "dynamic" coefficient of friction is the average of the values obtained during the 60 seconds of the test (6 inch travel distance). The testing apparatus may be a LAB MASTER Slip and Friction Model 32-90 with a model number 32-90-06 test sled; both of which are available from Testing Machines, Inc. of Islanda, N.Y., 11722, U.S.A.

The sled used for the testing may have a weight of 200 grams. Testing occurs in a room having a temperature of between about 22° C. and about 24° C., and a relative humidity of about 50%. The test material is mounted to the platen (table) had a length of about 305 millimeters and a width of about 102 to 127 millimeters using a double-sided tape. The test specimen has a length of about 100 millimeters and a width of about 63 millimeters. The sled is lowered by the test equipment before testing and positioned lightly onto the test material when the test was started to prevent any unnatural bond from developing. The length of the sled and the length the plane-mounted are parallel. The moving platen is then put in motion at a velocity of 6 inches per minute. The gauge takes readings and continues to do so for about 60 seconds (6 inches of travel). The gauge measures and stored the "static" value for the highest instantaneous coefficient of friction value obtained to begin the movement between the surfaces within the first inch of pull. The "dynamic" value is obtained and stored as the average of the values obtained during the 60 seconds of the test (6 inch travel distance).

The coefficient of friction evaluation was performed five times for each sample.

Example 1

A polyolefin composition was formed that contained 88 wt. % of PP 3155 (ExxonMobil), 5 wt. % of L-MODU™ 5400 (Idemitsu), 5 w. % of Exxon Vistamaxx™ 7050 and 2 wt. % of erucamide. PP 3155 (ExxonMobil) is a rigid propylene homopolymer having a density of 0.9 g/cm³, melting temperature of about 165° C., and a tensile modulus of about 1300 to 2000 MPa. L-MODU™ 5400 (Idemitsu) is a ductile propylene homopolymer having a density of 0.87 g/cm³, melting temperature of 70° C., tensile modulus of 80 MPa, and a melt flow rate of 2.000 g/10 min (230° C., 2.16 kg). The polyolefin composition was spun to form a nonwoven web using the following conditions: pump speed of 13.7 rpm, throughput of 100 kg/hr, melt temperature of 225° C., (FDU) Fiber Drawing Unit pressure of 0.50 bar, and process air temperature of 20° C. The resulting nonwoven web had a total basis weight of 15 gsm.

Example 2

A nonwoven web was formed as described in Example 1, except that the polyolefin composition was 88 wt. % of PP 3155 (ExxonMobil), 5 wt. % of L-MODU™ S400 (Idemitsu), 5 w. % of Vistamaxx™ 2330 and 2 wt. % of erucamide.

Example 3

A nonwoven web was formed as described in Example 1, except that the polyolefin composition was 88 wt. % of PP 3155 (ExxonMobil), 10 wt. % of L-MODU™ S400 (Idemitsu), and 2 wt. % of erucamide.

Example 4

A nonwoven web was formed as described in Example 1, except that the polyolefin composition was 93 wt. % of PP 3155 (ExxonMobil), 5 wt. % of L-MODU™ S400 (Idemitsu), and 2 wt. % of erucamide. The abrasion resistance (Martindale), softness (Cup Crush), and tensile properties (Peak Load and Elongation) of the samples formed according to Examples 1-4 were then tested as described above. The results are set forth in Tables 1-3 below.

TABLE 1

Martindale Abrasion Resistance

| | Abrasion 10 cycles @ 9 kPa | |
|---|---|---|
| Example | Rating No. | Std. Deviation |
| 1 | 5 | 1 |
| 2 | 5 | 1 |
| 3 | 5 | 0 |
| 4 | 5 | 0 |

TABLE 2

Cup Crush Softness

| | Cup Crush | | | |
|---|---|---|---|---|
| | Peak Load (gf) | | Total Energy (gf * mm) | |
| Example | Avg. | Std. Dev. | Avg. | Std. Dev. |
| 1 | 56.45 | 3.10 | 1019.22 | 89.98 |
| 2 | 58.64 | 4.14 | 1085.34 | 64.48 |
| 3 | 73.44 | 9.84 | 1384.63 | 158.82 |
| 4 | 107.64 | 7.51 | 2001.86 | 118.44 |

TABLE 3

| | Tensile Properties | | | | | | | |
|---|---|---|---|---|---|---|---|---|
| | MD | | | | CD | | | |
| | Peak Load (gf) | | Peak Elongation (%) | | Peak Load (gf) | | Peak Elongation (%) | |
| Example | Avg. | Std. Dev. | Avg. | Std. Dev. | Avg. | Std. Dev. | Avg. | Std. Dev. |
| 1 | 3808.90 | 357.22 | 37.7 | 3.8 | 1324.76 | 84.62 | 46.0 | 7.9 |
| 2 | 3249.10 | 149.59 | 31.0 | 1.7 | 1527.03 | 197.30 | 44.1 | 4.9 |
| 3 | 3401.39 | 107.44 | 32.7 | 1.1 | 1526.31 | 162.23 | 47.4 | 5.0 |
| 4 | 4175.17 | 276.63 | 43.7 | 4.0 | 2043.65 | 136.09 | 51.6 | 1.6 |

While the invention has been described in detail with respect to the specific embodiments thereof, it will be appreciated that those skilled in the art, upon attaining an understanding of the foregoing, may readily conceive of alterations to, variations of, and equivalents to these embodiments. The scope of the invention should be assessed as that of the appended claims and any equivalents thereto.

What is claimed is:

1. A nonwoven web comprising a plurality of fibers formed from a polyolefin composition, wherein the polyolefin composition contains
at least one rigid propylene polymer,
from about 0.5 wt. % to about 20 wt. % based upon the polyolefin composition of at least one ductile propylene polymer, and
from 0.5 wt. % to about 6 wt. % based upon the polyolefin composition of at least one slip additive, wherein a weight ratio of the at least one ductile propylene polymer to the slip additive is from about 1 to about 30, and
further wherein the ductile propylene polymer has a melt flow index of about 1,500 grams to about 5,000 grams per 10 minutes, and the rigid propylene polymer has a melt flow index of about 15 grams to about 80 grams per 10 minutes, as determined at a load of 2160 grams and at 230° C. in accordance with ASTM D1238-13.

2. The nonwoven web of claim 1, wherein the polyolefin composition has a melting temperature of from about 50° C. to about 145° C.

3. The nonwoven web of claim 1, wherein the rigid propylene polymer has a modulus of elasticity of from about 800 to about 4,000 MPa, as determined in accordance with ASTM D638-10.

4. The nonwoven web of claim 1, wherein the rigid propylene polymer is an isotactic homopolymer.

5. The nonwoven web of claim 1, wherein the rigid propylene polymer constitutes from about 75 wt. % to about 99.5 wt. % of the polyolefin composition.

6. The nonwoven web of claim 1, wherein the ratio of the modulus of elasticity of the rigid propylene polymer to the modulus of elasticity of the ductile propylene polymer is from about 1 to about 50, as determined in accordance with ASTM D638-10.

7. The nonwoven web of claim 6, wherein the modulus of elasticity of the ductile propylene polymer is from about 1 to about 500 MPa, as determined in accordance with ASTM D638-10.

8. The nonwoven web of claim 1, wherein the ductile propylene polymer has a melting temperature of from about 40° C. to about 120° C.

9. The nonwoven web of claim 1, wherein the ductile propylene polymer has a degree of crystallinity of from about 1% to about 35%, as determined using differential scanning calorimetry in accordance with ASTM D-3417.

10. The nonwoven web of claim 1, wherein the ductile propylene polymer is a metallocene-catalyzed homopolymer.

11. The nonwoven web of claim 1, wherein the ductile propylene polymer constitutes from about 0.5 wt. % to about 15 wt. % of the polyolefin composition and/or the slip additive constitutes from 0.5 wt. % to about 3 wt. % of the polyolefin composition.

12. The nonwoven web of claim 1, wherein the slip additive includes a fatty acid derivative, and preferably a fatty acid amide, such as erucamide, oleamide, or a combination thereof.

13. The nonwoven web of claim 1, wherein the fibers have a denier of from about 3 or less.

14. The nonwoven web of claim 1, wherein the nonwoven web is a spunbond web.

15. The nonwoven web of claim 1, wherein the nonwoven web exhibits a cup crush load of about 200 grams-force or less and/or a coefficient of friction in the machine direction of about 0.885 or less.

16. A composite comprising the nonwoven web of claim 1 and at least one additional layer.

17. The composite of claim 16, wherein the additional layer includes a second nonwoven web that contains a plurality of fibers formed from a second polyolefin composition, wherein the second polyolefin composition contains at least one ethylene polymer.

18. The composite of claim 16, wherein the nonwoven web constitutes from about 20 wt. % to about 80 wt. % of the composite and the additional layer constitutes from about 20 wt. % to about 80 wt. % of the composite.

19. The composite of claim 16, wherein the additional layer includes a film.

20. An absorbent article comprising an absorbent core positioned between a backsheet and a topsheet, wherein the backsheet, topsheet, or both contains the nonwoven web of claim 1.

21. The nonwoven web of claim 1, wherein the at least one ductile propylene polymer comprises at least one ductile propylene homopolymer.

* * * * *